United States Patent [19]

Brown et al.

[11] Patent Number: 5,571,142
[45] Date of Patent: Nov. 5, 1996

[54] NON-INVASIVE MONITORING AND TREATMENT OF SUBJECTS IN CARDIAC ARREST USING ECG PARAMETERS PREDICTIVE OF OUTCOME

[75] Inventors: Charles G. Brown; Roger R. Dzwonczyk, both of Columbus, Ohio

[73] Assignee: The Ohio State University Research Foundation, Columbus, Ohio

[21] Appl. No.: 298,376

[22] Filed: Aug. 30, 1994

[51] Int. Cl.⁶ .............................. A61B 5/046; A61N 1/39
[52] U.S. Cl. ........................ 607/5; 128/200.24; 128/705
[58] Field of Search ..................... 128/696, 697, 128/702, 704, 705, 708, 200.24; 607/5, 7; 364/413.05, 413.06

[56] References Cited

U.S. PATENT DOCUMENTS 4,296,755  10/1981  Judell ........................ 128/705
4,680,708   7/1987  Ambos et al. ............... 364/413.06
4,974,162  11/1990  Siegel et al. ................ 364/413.06
5,077,667  12/1991  Brown et al. ............... 364/413.05
5,092,341   3/1992  Kelen ........................ 364/413.06 X Primary Examiner—William E. Kamm
Assistant Examiner—Jeffrey R. Jastrzab
Attorney, Agent, or Firm—Van Dyke, Gardner, Linn & Burkhart, LLP

[57] ABSTRACT

A method and apparatus for determining the metabolic state of the myocardium of a subject in ventricular fibrillation or asystole and/or for guiding therapeutic interventions. Electrocardiogram signals of the subject's heart are transformed to a frequency domain power spectrum, and at least one frequency parameter is monitored and processed to a value predictive of a clinically relevant cardiac arrest outcome. In the preferred embodiment, centroid frequency and/or peak power frequency of the power spectrum are monitored.

44 Claims, 13 Drawing Sheets

NON-INVASIVE MONITORING AND TREATMENT OF SUBJECTS IN CARDIAC ARREST USING ECG PARAMETERS PREDICTIVE OF OUTCOME

BACKGROUND OF THE INVENTION

This invention relates generally to the monitoring and treatment of a human or animal subject in cardiac arrest from the electrocardiogram (ECG) of the subject's heart. More particularly, the invention is related to determining clinically useful parameters from the subject's ECG which help guide therapeutic interventions during ventricular fibrillation. As used herein, ventricular fibrillation is intended to include asystole which may be considered a form of ventricular fibrillation.

Each year more than 350,000 sudden cardiac deaths occur in the United States. The successful development and implementation of emergency medical services has resulted in saving many of these subjects. Training the public to perform basic lifesaving maneuvers, like cardiopulmonary resuscitation (CPR), as well as providing easy and early access to medical help, which provides skilled rescuers at the subject's location within minutes of the arrest, has saved lives. However, survival from out-of-hospital cardiac arrest is much lower than theoretically possible. Even the advent of automatic and semi-automatic external defibrillators, and their widespread use by first responders to victims of sudden cardiac arrest, has had only a modest impact on survival.

Although electrical countershock is the most effective treatment of ventricular fibrillation, there is biochemical, histological, and clinical evidence to suggest that electrical countershock can cause myocardial injury. When the duration of ventricular fibrillation is prolonged and the heart is not metabolically conducive to countershock administration, the cumulative energy applied from unsuccessful countershocks to the fibrillating myocardium may impair subsequent efforts at successfully converting the heart to a pulsatile rhythm, that is a cardiac rhythm that allows effective perfusion to the subject. Thus, after more prolonged durations of ventricular fibrillation, therapy aimed at improving myocardial perfusion and, thus, the metabolic state of the myocardium, prior to countershock administration, appears to optimize outcome.

In our U.S. Pat. No. 5,077,667 entitled MEASUREMENT OF THE APPROXIMATE ELAPSED TIME OF VENTRICULAR FIBRILLATION AND MONITORING THE RESPONSE OF THE HEART TO THERAPY, we disclosed a technique for accurately estimating the elapsed time of a subject in ventricular fibrillation. In our patent, time domain samples of the subject's electrocardiogram (ECG) signal are transformed to a frequency domain spectrum and the median frequency, which bisects the energy of the power spectrum, is detected. The median frequency is compared with a pattern of experimentally obtained median frequency data to estimate the elapsed time of ventricular fibrillation. This information may be used to establish the most appropriate time to countershock a subject.

Estimation of the elapsed time of ventricular fibrillation can be affected by many factors. These include whether the subject received cardiopulmonary resuscitation prior to the time that the measurement was made and the degree of perfusion of the heart. For example, the subject may be in cardiac arrest clinically but still have some degree of myocardial perfusion when the heart is in a rhythm called "ventricular tachycardia" or "Torsades de Pointes." Thus, when cardiopulmonary resuscitation generates adequate myocardial perfusion, or if the subject is in a condition with some degree of myocardial perfusion, the metabolic state of the myocardium may not deteriorate as rapidly, despite the fact that the subject is in cardiac arrest clinically. Accordingly, it is desirable to provide a more accurate determination of the metabolic state of the myocardium which takes into account the level of myocardial perfusion prior to measurement of the metabolic state of the myocardium. It is additionally desirable to more accurately predict whether attempts to countershock the subject will result in conversion of the heart to an organized, pulsatile rhythm, in order to avoid the application of unnecessary and potentially harmful countershocks. It is additionally desirable to provide a non-invasive method of guiding therapeutic interventions during ventricular fibrillation and asystole.

SUMMARY OF THE INVENTION

According to one aspect, the invention provides a non-invasive method of guiding therapeutic interventions to a subject in cardiac arrest. The method includes connecting electrodes to the body of the subject and detecting from the electrodes an analog electrical potential which is proportional to the electrical potential generated by the subject's heart. The analog potential is sampled for a selected interval of time to obtain a set of time domain samples. A power distribution of the electrical potential is detected by transforming the time domain samples to a frequency domain power spectrum. At least one amplitude parameter of the ECG time-domain signal interval and/or frequency parameter of the power spectrum is determined and monitored. These parameter or parameters are predictive of a clinically relevant cardiac arrest outcome for the subject. Therapy is administered to the subject as a function of the value of such parameter or parameters.

According to a more detailed aspect of the invention, one of the parameters that is predictive of clinically relevant cardiac arrest outcome for the subject is the centroid frequency ($F_c$) of the power spectrum. According to another more detailed aspect of the invention, another of the parameters that is predictive of clinically relevant cardiac arrest outcome for the subject is the peak power frequency ($F_p$) of the power spectrum. In a most preferred form, the combined values of the centroid frequency and the peak power frequency are used as predictive of such cardiac arrest outcomes.

According to another aspect of the invention, a non-invasive method of determining myocardial perfusion and, thus, the metabolic state of the myocardium of a subject in ventricular fibrillation or asystole includes connecting electrodes to the body of the subject and detecting from the electrodes an analog electrical potential which is proportional to the electrical potential generated by the subject's heart. The analog potential is sampled for a selected interval of time to obtain a set of time domain samples and the power distribution of the electrical potential is detected by transforming the time domain samples to a frequency domain power spectrum. At least one amplitude parameter of the ECG time-domain signal interval and at least one frequency parameter of the power spectrum is determined and monitored, such parameter or parameters being predictive of a clinically relevant cardiac arrest outcome for the subject. These parameter or parameters are resolved to provided an indication of the metabolic state of the myocardium of the subject's heart. Preferably, the predictive parameter is selected from a group of parameters including centroid frequency of the power spectrum ($F_c$) and peak power frequency of the power spectrum ($F_p$). The method according to this aspect of the invention may further include applying therapy to a subject in ventricular fibrillation or asystole, assessing the effect of the therapy on the subject utilizing the determined parameter from the subject's ECG, and guiding further therapy based upon the assessment. The method may further include prescribing a particular therapeutic protocol as a function of centroid frequency and/or peak power frequency of the power spectrum.

Other aspects of the invention are embodied in an apparatus that noninvasively establishes a clinically useful characteristic of the heart of a subject in ventricular fibrillation or asystole from an electrocardiogram of the heart. The apparatus includes an analyzer for determining at least one amplitude parameter of the ECG time-domain signal interval and frequency parameter of the power spectrum of the ECG, with the parameter being predictive of a clinically relevant cardiac arrest outcome for the subject and the metabolic state of the myocardium. A processor is provided for resolving the parameter or parameters to a clinically useful characteristic of the subject's heart. The apparatus may be used as a monitor alone or in combination with a defibrillator for administering countershocks or other resuscitators in response to a value of the parameter or combination of parameters.

These and other objects, advantages, and features of this invention will become apparent upon review of the following specification in conjunction with the drawings.

DESCRIPTION OF THE PREFERRED EMBODIMENT

Figure 1:
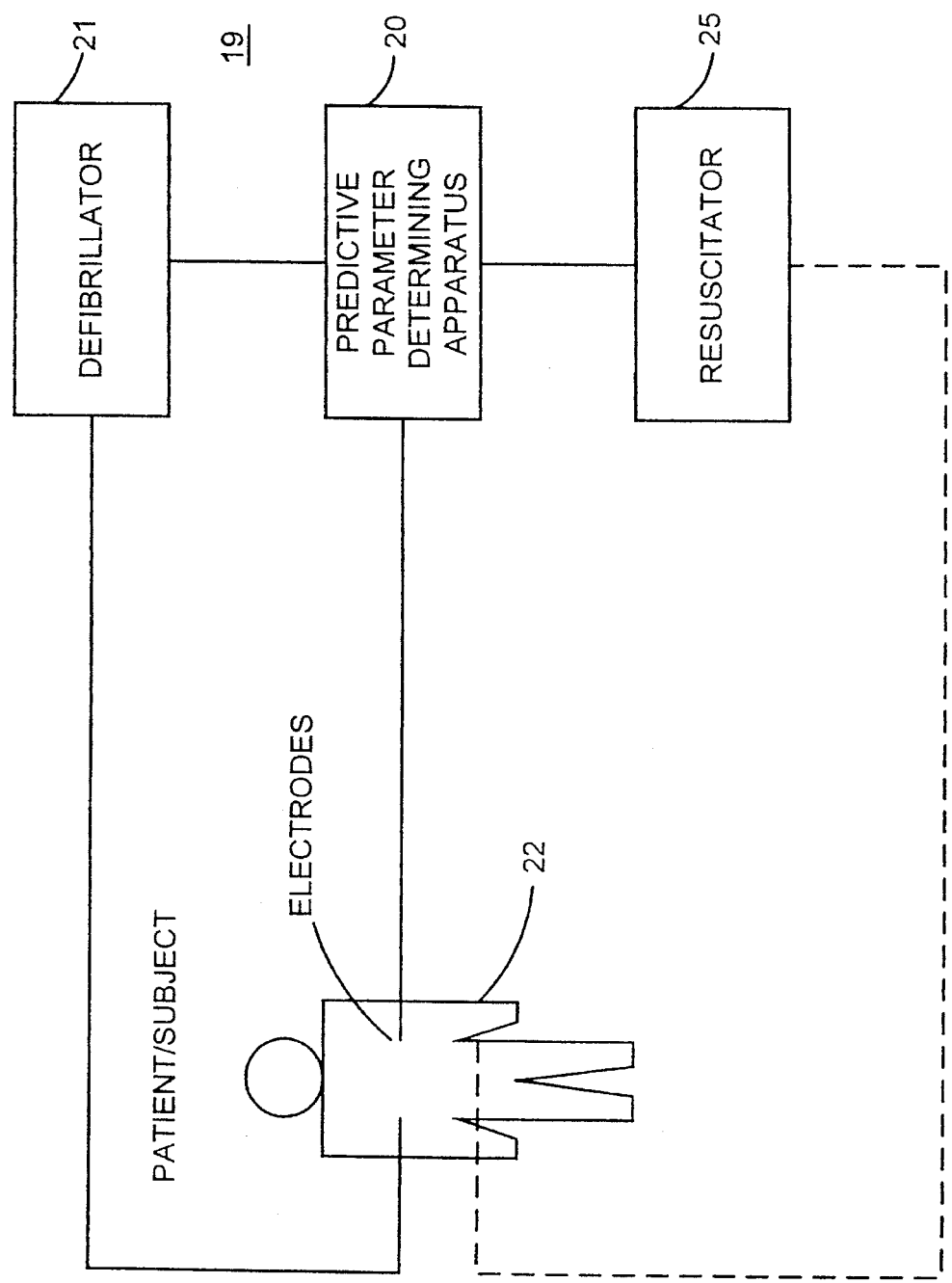
FIG. 1 is a block diagram of an apparatus according to the invention connected with a subject.
Figure 2:
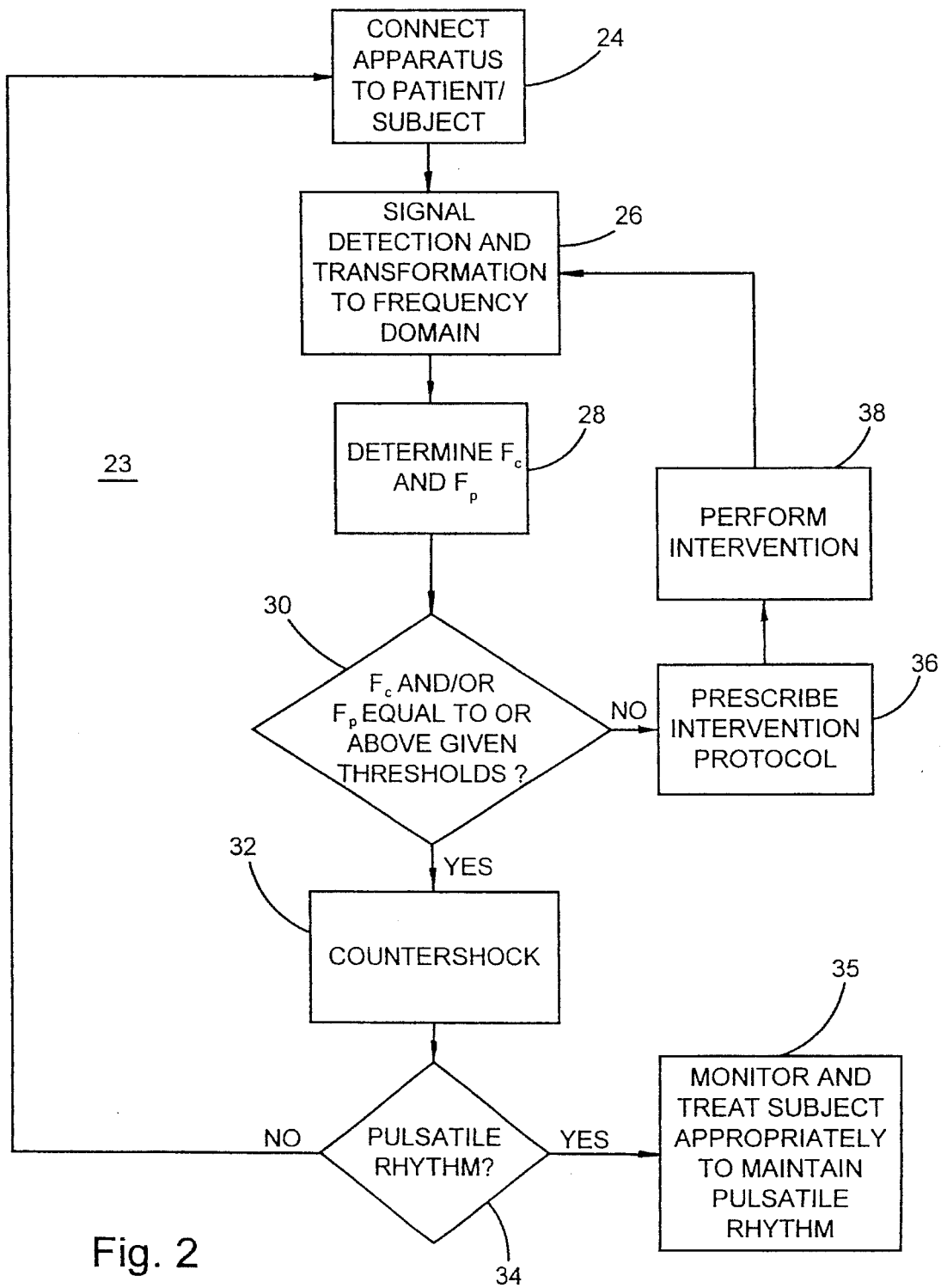
FIG. 2 is a flowchart of a method of treating a subject in ventricular fibrillation, according to the invention.

Referring specifically to the drawings, and the illustrative embodiments depicted therein, an apparatus 19, including a predictive parameter determining apparatus 20 and/or a defibrillator 21, and/or a resuscitator 25, is connected to a subject 22, who is assessed to be in cardiac arrest, utilizing conventional internal or external electrodes (FIG. 1). After the apparatus is connected to the subject at 24, a method 23 of treating the subject with apparatus 19 is performed (FIG. 2). Method 23 includes detecting an analog electrical potential which is proportional to the electrical potential generated by the subject's heart and transforming the analog signal into the frequency domain utilizing a fast Fourier transform algorithm, at 26. The technique for converting the analog signal into the frequency domain is disclosed in U.S. Pat. No. 5,077,667 issued to Charles G. Brown and Roger Dzwonczyk, the disclosure of which is hereby incorporated herein by reference and will not be repeated. The centroid frequency ($F_c$) and the peak power frequency ($F_p$) of the power spectrum are determined at 28. The centroid frequency is defined as the X-axis (frequency) coordinate of the center of spectral mass and it is determined by:

$$F_c = \frac{\sum_{i=1}^{n} (f_i \cdot p_i)}{\sum_{i=1}^{n} p_i}$$

Where $f_1$ equals the ith frequency component and $p_i$ equals the power at $f_i$. Peak power frequency ($F_p$) is the frequency that has the peak power in the power spectrum. The parameters, $F_c$ and $F_p$, are reported in Hertz and provide an estimate of the frequency distribution of the power of a signal in the spectrum.

After $F_c$ and $F_p$ are determined by predictive parameter determining apparatus 20, it is then determined at 30 whether $F_c$ and/or $F_p$ are equal to or above particular thresholds. In the illustrated embodiment, the threshold for $F_p$ may be set in the range between approximately 3.5 Hz and approximately 7.75 Hz and the threshold for $F_c$ may be set in the range between approximately 3.86 Hz and approximately 6.12 Hz. These threshold values are applicable to human subjects and may be different for other species. If $F_c$ and/or $F_p$ are equal to or above their respective thresholds, defibrillator 21 is instructed by apparatus 20 at 32 to issue a countershock. It is then determined at 34 whether the countershock resulted in conversion of the ventricular fibrillation to a pulsatile rhythm. If not, then the above-identified procedure is repeated. If conversion to a pulsatile rhythm is achieved, subject 22 is monitored and treated at 35 in order to maintain a pulsatile rhythm. If subject 22 is determined at any time not to have a pulsatile rhythm at 35, the ECG signal from subject 22 is again processed at 26.

If it is determined at 30 that both of the parameters $F_c$ and $F_p$ are below their respective thresholds, then a non-countershock therapy may be instituted at 36. In a preferred form, the alternative therapy is chosen as a function of the value of $F_c$ and/or $F_p$. Such alternative therapy may include utilizing drugs, manual cardiopulmonary resuscitation, mechanical resuscitation through the use of resuscitator 25, and/or ventilation/oxygenation.

The prescribed intervention is carried out at 38. The electrical potential generated by the subject's heart can be continuously sampled at 26 and processed to obtain the value of $F_c$ and/or $F_p$. The intervention protocol is either changed, modified, or kept the same at 36 and carried out at 38. In this manner, the therapy may be titrated to achieve the appropriate values of the parameters $F_c$ and/or $F_p$. When the predetermined threshold values of $F_c$ and/or $F_p$ are reached or exceeded at 30, as a result of titrating the therapy to the subject (26, 28, 30, 36, 38), a countershock may be administered at 32.

Thus, method 23 may be utilized to select the type and dosage of a drug. Method 23 may also be used to determine an optimum rate, force, and/or depth of compression of manual or mechanical CPR, or to select the compression-to-ventilation ratio of concurrent subject ventilation. Method 23 may be utilized for optimizing all forms of cardiopulmonary resuscitation, such as closed-chest CPR, open-chest cardiopulmonary resuscitation, and CPR which utilizes any mechanical adjunct. In this manner, method 23 may be utilized with mechanical resuscitators, ventricular assist devices, and cardiopulmonary bypass techniques performed during open-heart procedures. Thus, method 23 provides a feedback loop to monitor myocardial perfusion, titrate therapy, and optimize perfusion techniques during all forms of CPR.

Method 23 may also be utilized to select a defibrillation threshold, which is defined as the minimum amount of energy and/or current required to convert the cardiac rhythm from a ventricular fibrillation to a non-ventricular fibrillation rhythm. Thus, a determination of the minimum amount of energy or current a defibrillator needs to deliver could be derived as a function of the value of $F_c$ and/or $F_p$. This could help minimize myocardial injury and also save energy for the battery of defibrillators. Method 23 may also be used to estimate the optimum waveform and/or paddle position to use when delivering a countershock. Method 23 may be used to treat subjects experiencing involuntary cardiac arrest, but may also be used to restart a heart that has been intentionally placed into ventricular fibrillation for cardio-vascular surgery or the like. Although the heart is perfused during surgery, lactic acid and other products may accumulate in the myocardium. Method 23 provides a technique for ensuring optimum perfusion and that non-productive countershocks will not be administered.

Figure 3:
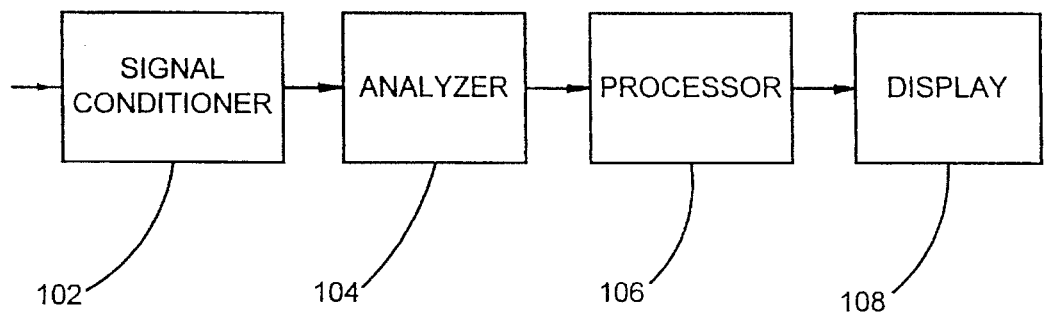
FIG. 3 is a block diagram of the apparatus in FIG. 1.

A subject monitor apparatus 100 includes an analyzer 104 for determining at least one amplitude parameter of the ECG time-domain signal interval or frequency parameter of a power spectrum following fast Fourier analysis of the subject's ECG (FIG. 3). Conditioning unit 102 amplifies, filters, and digitizes the subject's ECG. A processor 106 resolves the values of the parameter or parameters determined by analyzer 104 into clinically useful characteristics of the subject's heart, which may be displayed on display 108, along with the values of the parameters themselves, if desired. Signal conditioner 102 may be provided by an external apparatus, such as an ECG monitor or a defibrillator, or may be included with apparatus 100. Apparatus 100 may be useful tier a research monitor to display the results of experimental interventions on animal or human subjects or as a subject monitor to read out vital characteristics of the heart of a subject in an emergency room, critical care unit, or the like.

Figure 4:
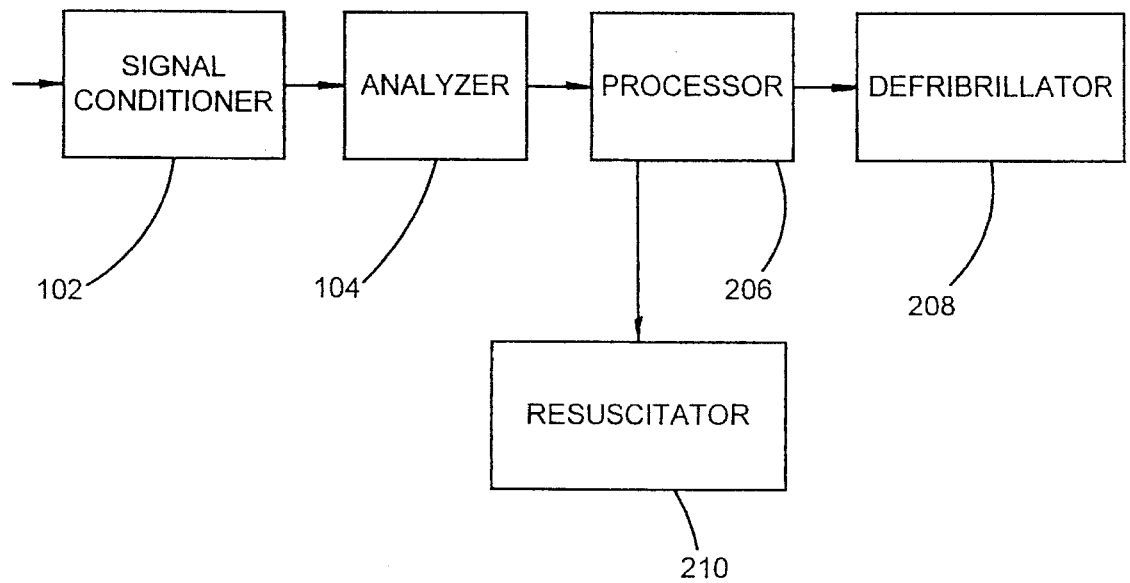
FIG. 4 is a block diagram of an alternative apparatus, according to the invention.

A treatment apparatus 200 is provided that includes a processor 206 that is capable of making a determination to administer an electrical countershock and to control a defibrillator 208 in applying the countershock to the subject (FIG. 4). This may include the timing, energy, current, waveform, or the like, of the countershock. Apparatus 200 may additionally include an output for controlling a resuscitator 210 or other mechanical-administering adjunct. Apparatus 200 may be built into defibrillator 208 in a compact housing along with a microcomputer to carry out the functions of conditioner 102, analyzer 104, and processor 206, or may be a separate unit. The above example is for illustration purposes only. It should be understood that apparatus 200 may include only a defibrillator, 208, only a resuscitator, 210, or both.

Other functions may be included with apparatus 100, 200. For example, an event marker may be included in order to allow a particular event to be time-stamped in the apparatus, such as a drug administration or the like.

Thus, it is seen that the present invention provides a method and an apparatus that may be incorporated into existing ECG monitors and/or defibrillators in order to provide manual, semi-automatic, or automatic subject treatment devices, as well as to be used as a stand-alone monitor. The invention may be applied to subjects of all species, habitus, underlying pathophysiology, and duration of ischemia. Because the invention includes a reliable procedure for determining the ability of the subject's heart to be converted to a pulsatile rhythm following countershock, damage to the myocardium resulting from cumulative energy from one, or a succession, of countershocks may be avoided. The present invention additionally provides the ability to regulate .the level of therapeutic interventions and, thereby, avoid damage from unnecessary interventions or interventions greater than that required. The invention additionally provides the ability to accurately monitor myocardial perfusion and, thus, the metabolic state of the subject's heart based upon the recognition that $F_c$ is positively correlated with myocardial perfusion pressure during CPR. Since $F_c$ and $F_p$ are predictive of successful outcomes from countershock which is dependent upon myocardial perfusion, then $F_p$ should also be positively correlated with myocardial perfusion pressure during CPR. The parameters $F_c$ and $F_p$ in combination provide an especially reliable prediction of the ability of the subject's heart to be converted to a pulsatile rhythm following countershock.

EXAMPLE

A retrospective analysis of ECG cassette recordings obtained during cardiac arrest of 55 human subjects with out-of-hospital cardiac arrest whose initial ECG rhythms were identified as ventricular fibrillation. Subjects were monitored with a semi-automatic defibrillator/ECG monitor equipped with an ECG and voice cassette recording, such as Model "HEART AID" 1000, "HEARTSTART" 1000, or "HEARTSTART" 2000 marketed by Laerdal Corporation in Armonk, N.Y. The frequency bandwidth of the ECG recording was 1.7–20 Hz. The recorded ECG signals were digitized with an analog-to-digital converter, Model No. DT-2801A marketed by Data Translation, of Marlborough, Mass. The analog-to-digital conversion was done at 64 Hz and analyzed on an IBM compatible microcomputer utilizing a program written in commercial scientific software package language "ASYST", Version 4.01, marketed by Keithley Instrument Company in Taunton, Mass. The ECG signals were processed in the same manner disclosed in U.S. Pat. No. 5,077,667 to Charles G. Brown and Roger Dzwonczyk. Each electrical countershock was identified on the ECG recording and a four-second epoch just prior to each countershock was analyzed. Each time-domain signal epoch was transformed into the frequency domain using a fast Fourier transform algorithm. Centroid frequency ($F_c$) and peak power frequency ($F_p$) were extracted from the resulting power spectrum. Average segment amplitude (SA) and average wave amplitude (WA) were extracted from the original time domain ECG epoch. The portion of the ventricular fibrillation ECG signal extending from peak to the following adjacent trough is defined as a "wave." Wave amplitude is the difference between the peak and trough amplitude of a wave. The average wave amplitude was obtained by calculating the average of all peak-to-trough wave amplitudes in the epoch. The average segment amplitude was obtained by calculating the average of the full-wave rectified signal epoch. To be included in the calculation of WA, the peak and trough must have been at least 0.256 seconds apart in time. The parameters WA and SA are reported in microvolts and provide an estimate of the average amplitude of a time-domain signal in the epoch.

The result of each countershock was also recorded and paired with the corresponding parameter values. A successful countershock was defined as the conversion of ventricular fibrillation to a supraventricular rhythm associated with a palpable pulse or blood pressure of any duration within two minutes of the countershock without ongoing CPR. Emergency Medical Services' (EMS) records were reviewed retrospectively to determine the result of each countershock. A countershock was eliminated from analysis if the ECG signal prior to the countershock contained identifiable artifact, such as interference from cardiopulmonary resuscitation, or other noise. The subjects received a total of 324 countershocks. However, only 128 of the countershocks were free of artifact. Nine of the 128 countershocks considered were successful, namely they resulted in conversion to a pulsatile rhythm. Each countershock was analyzed as an independent event. The mean, range, and median values for each parameter were determined for unsuccessful and successful countershocks. A Kolmogorov-Smirnov comparison was performed on the parameters $F_c$, $F_p$, SA; and WA in relation to countershock success, return of spontaneous circulation at any later time, survival to admission to hospital, and survival to discharge from hospital.

Figure 5:
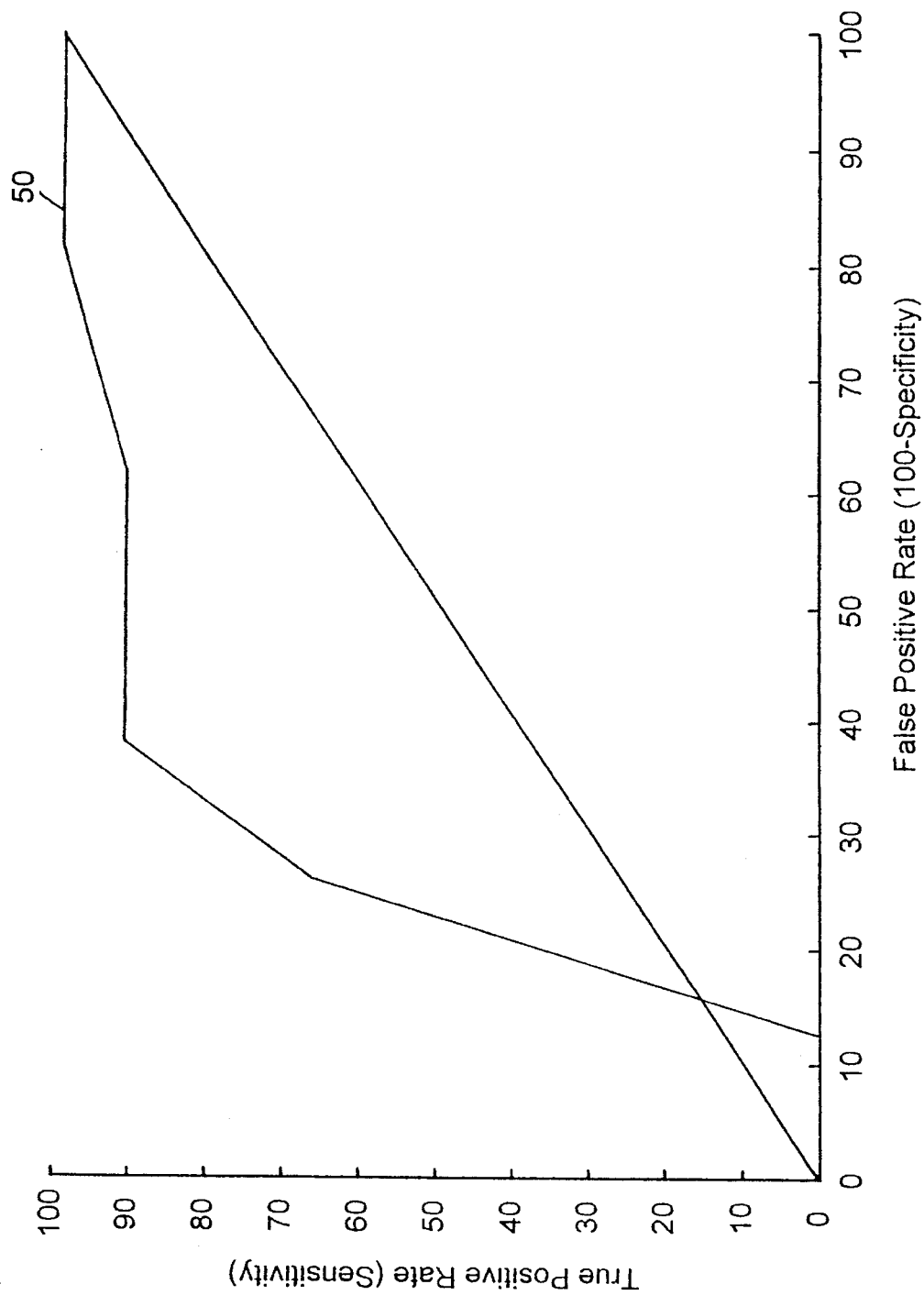
FIG. 5 is a graph illustrating a receiver operating characteristic curve of the centroid frequency of the power spectrum for an outcome of successful countershock.
Figure 6:
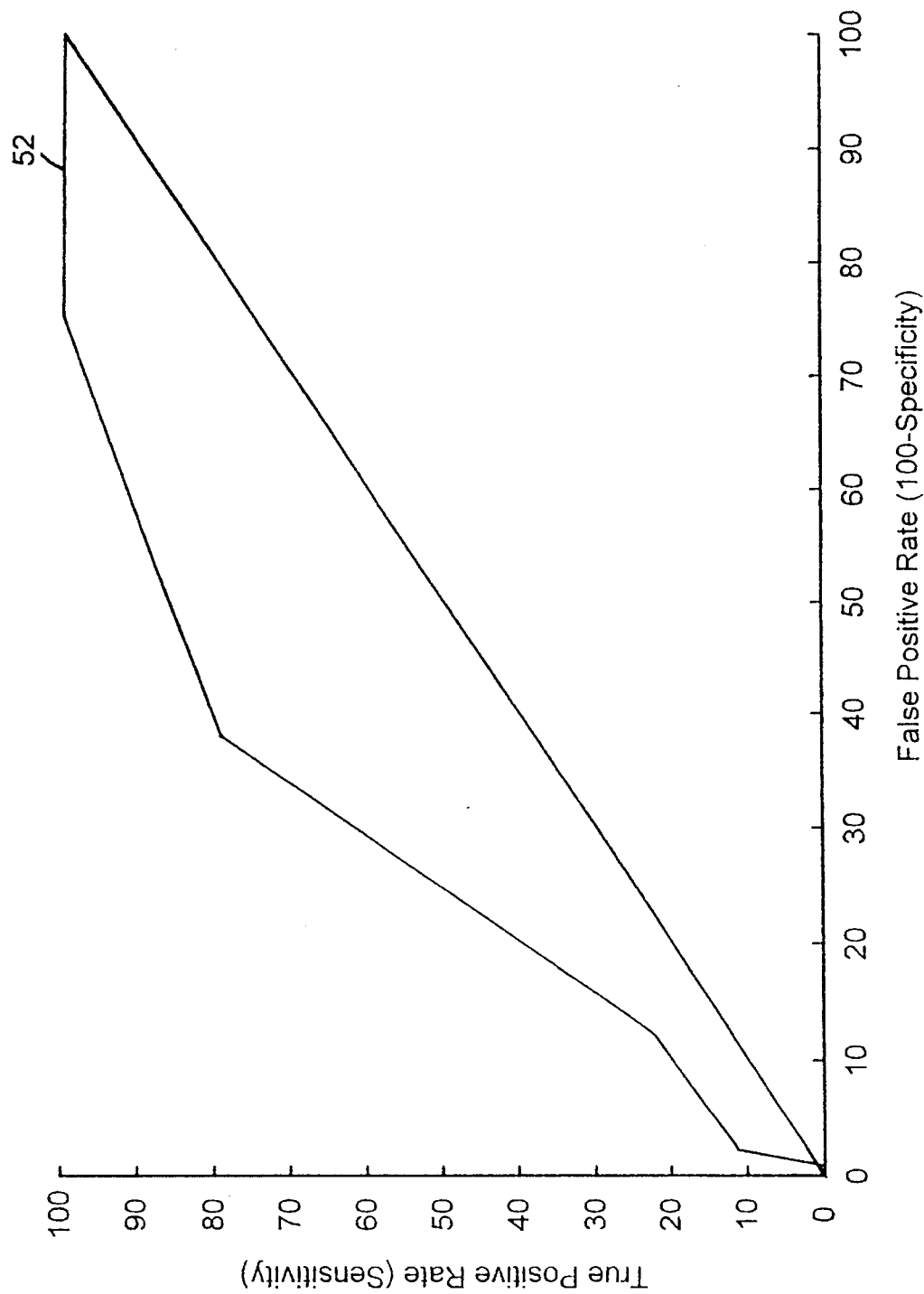
FIG. 6 is a graph illustrating a receiver operating characteristic curve of the peak power frequency of the power spectrum for an outcome of successful countershock.
Figure 7:
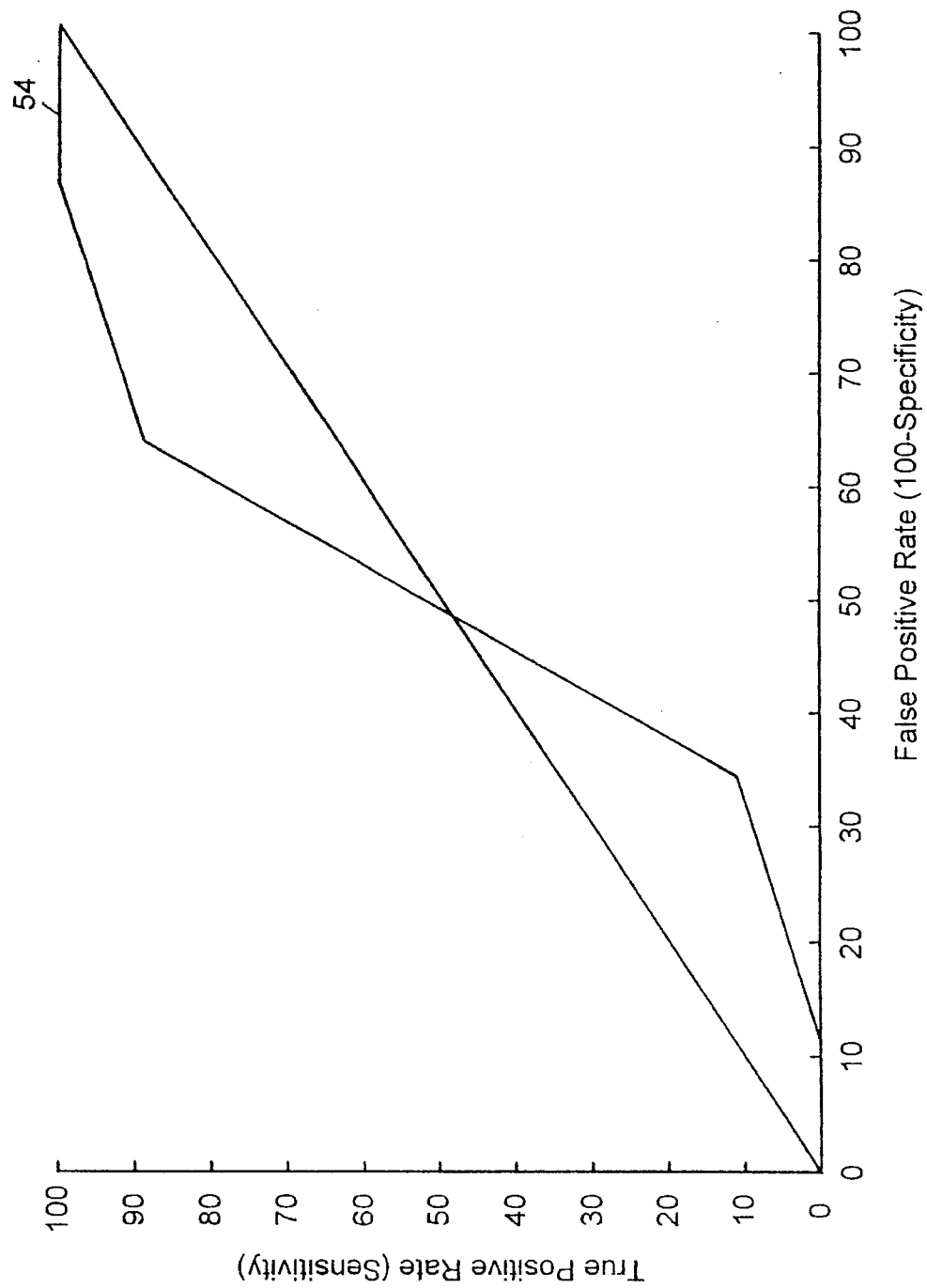
FIG. 7 is a graph illustrating a receiver operating characteristic curve of the average segment amplitude of the power spectrum for an outcome of successful countershock.
Figure 8:
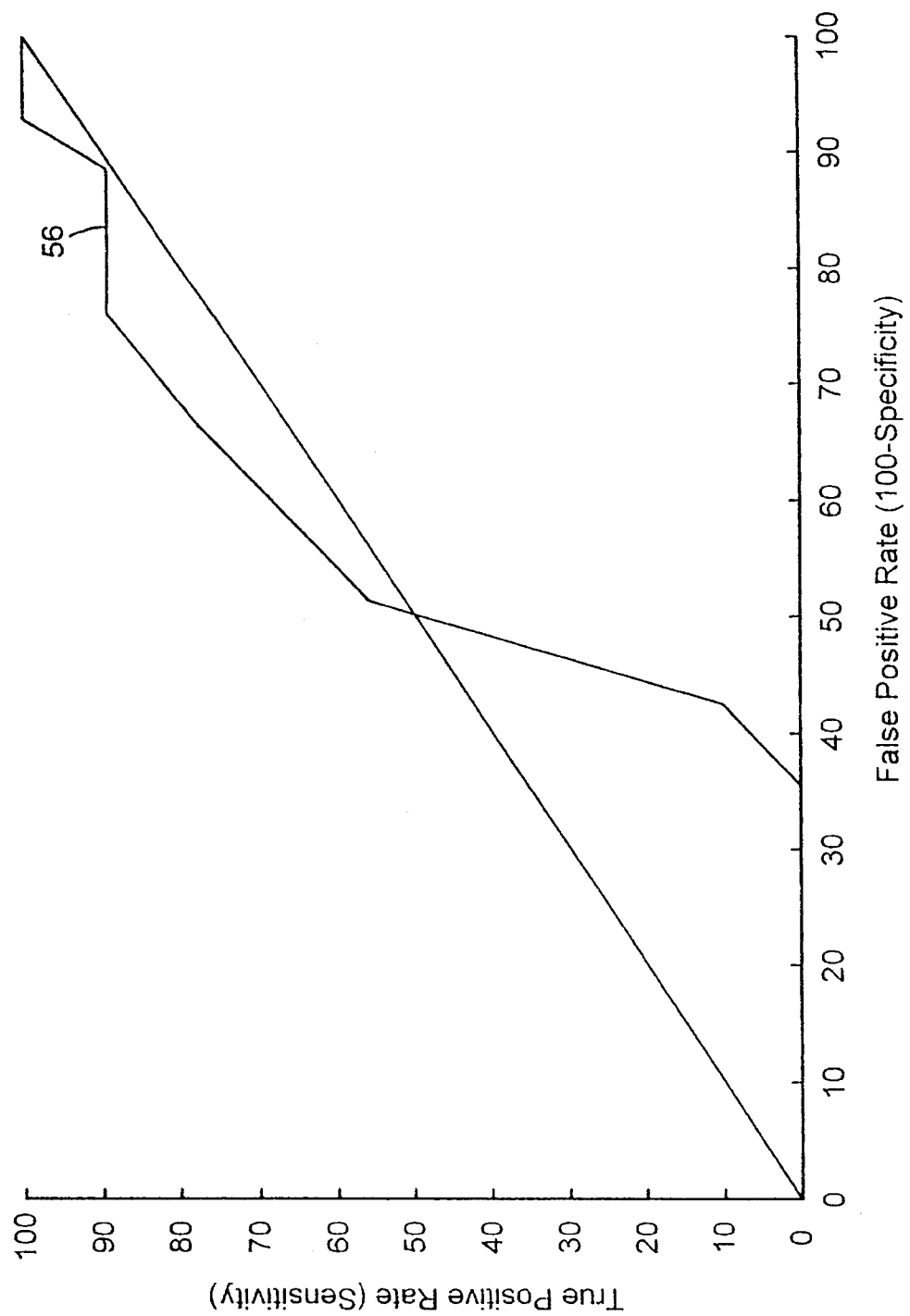
FIG. 8 is a graph illustrating a receiver operating characteristic curve of the average wave amplitude of the power spectrum for an outcome of successful countershock.

The value for determining 100% sensitivity and maximum specificity of each parameter alone, and in combination, was determined. The term "sensitivity" of the parameter is the probability that the parameter will be equal to or greater than a specific value given that the subject is successfully countershocked. The "specificity" of the parameter is the probability that the parameter will be less than a specific value given that the subject is not successfully countershocked. The value of each parameter as a predictor of clinically relevant cardiac arrest outcomes was determined by calculating the area under the receiver operating characteristic (ROC) curve. An ROC curve 50 of the parameter $F_c$ for an outcome of successful countershock is illustrated in FIG. 5. The area under ROC curve 50 represents the probability to which $F_c$ can be used to predict successful countershock. The area under curve 50 is 0.717. An ROC curve 52 of the parameter $F_p$ for an outcome of successful countershock is illustrated in FIG. 6. The area under ROC curve 52 represents the probability to which $F_p$ can be used to predict success. The area under curve 52 is 0.697. A review of FIGS. 5 and 6 illustrates the significant ability of the parameters to predict successful countershock of the subject. The significant area under ROC curves 50 and 52 is in contrast to ROC curve 54 of the parameter SA, for an outcome of successful countershock (FIG. 7), and ROC curve 56 of the parameter WA (FIG. 8) for an outcome of successful countershock. Curves 54 and 56 have significant negative as well as positive areas, which indicates the relatively low probability, of the parameters SA and WA, in and of themselves, to reliably predict successful countershock of the subject.

A statistical analysis for the parameters $F_c$, $F_p$, SA, and WA for a cardiac arrest outcome of successful countershock, which is defined for the purpose of this analysis to be the return of spontaneous circulation within two (2) minutes of the countershock, is shown in Table 1:

TABLE 1

| | COUNTERSHOCK OUTCOME | | | | | | |
|---|---|---|---|---|---|---|---|
| | SUCCESSFUL | | | UNSUCCESSFUL | | | P– |
| Parameter | Mean | Range | Median | Mean | Range | Median | Value |
| $F_c$ | 5.48 ± 0.67 | 3.86–6.12 | 5.66 | 4.85 ± 1.16 | 2.62–8.75 | 4.67 | 0.012 |
| $F_p$ | 5.31 ± 1.24 | 3.50–7.75 | 5.00 | 4.29 ± 1.63 | 0.25–11.0 | 4.00 | 0.066 |
| SA | 133 ± 32 | 70–180 | 142 | 132 ± 61 | 20–260 | 129 | 0.549 |
| WA | 386 ± 95 | 190–530 | 412 | 384 ± 184 | 50–800 | 366 | 0.337 |

It can be seen from Table 1 that the mean value of $F_c$ was significantly higher for successful countershock than for unsuccessful countershock, with P=0.012. The statistical difference for $F_p$ (P=0.066), SA (P=0.549), and WA (P=0.337) falls outside of the statistical significance of the test of P≦0.05. Further analysis also illustrates that, when the parameters $F_p$ and $F_c$ are used in combination and when the value of $F_p$ falls within the range of 3.5 Hz to 7.75 Hz and the parameter $F_c$ falls within the range of 3.86 Hz to 6.12 Hz, the combination has a sensitivity of 100% and a specificity of 47.1% in predicting successful countershock.

Table 2 illustrates a statistical analysis for the parameters $F_c$ and $F_p$ with a successful outcome defined as a return of spontaneous circulation more than two minutes after countershock:

TABLE 2

| | RETURN OF SPONTANEOUS CIRCULATION EVER | | | | | | |
|---|---|---|---|---|---|---|---|
| | SUCCESSFUL | | | UNSUCCESSFUL | | | P– |
| Parameter | Mean | Range | Median | Mean | Range | Median | Value |
| $F_c$ | 5.02 ± 1.10 | 2.62–8.75 | 4.97 | 3.96 ± 1.22 | 2.68–5.58 | 3.45 | 0.101 |
| $F_p$ | 4.63 ± 1.67 | 0.25–11.00 | 4.75 | 2.50 ± 0.57 | 1.75–3.00 | 2.75 | 0.003 |

It can be seen from Table 2 that the mean value of $F_p$ was significantly higher for successful return of spontaneous circulation at any later time than for unsuccessful return of spontaneous circulation at any later time, with P=0.003. The statistical difference for $F_c$ (P=0.101) falls outside of the statistical significance of the test.

Table 3 illustrates a statistical analysis for the parameters $F_c$ and $F_p$ with a successful outcome defined as a survival to admission to a hospital:

TABLE 3

SURVIVAL TO ADMISSION TO HOSPITAL

| Parameter | SUCCESSFUL | | | UNSUCCESSFUL | | | P-Value |
|---|---|---|---|---|---|---|---|
| | Mean | Range | Median | Mean | Range | Median | |
| $F_c$ | 5.22 ± 1.22 | 2.62–8.75 | 5.37 | 4.52 ± 0.92 | 2.68–6.91 | 4.51 | 0.001 |
| $F_p$ | 4.82 ± 1.89 | 0.25–11.00 | 4.75 | 3.83 ± 1.21 | 1.75–7.00 | 3.75 | 0.001 |

It can be seen from Table 3 that the mean values of both $F_c$ and $F_p$ were significantly higher for successful survival to admission to hospital than for unsuccessful, with P=0.001 for each.

Table 4 illustrates a statistical analysis for the parameters $F_c$ and $F_p$ with a successful outcome defined as a survival to discharge from a hospital:

TABLE 4

SURVIVAL TO DISCHARGE FROM HOSPITAL

| Parameter | SUCCESSFUL | | | UNSUCCESSFUL | | | P-Value |
|---|---|---|---|---|---|---|---|
| | Mean | Range | Median | Mean | Range | Median | |
| $F_c$ | 6.17 ± 0.38 | 5.63–6.73 | 6.10 | 4.64 ± 1.03 | 2.62–6.91 | 4.63 | 0.0001 |
| $F_p$ | 6.00 ± 1.15 | 4.00–7.75 | 5.88 | 4.05 ± 1.38 | 1.75–7.75 | 3.75 | 0.002 |

It can be seen from Table 4 that the mean value of both $F_c$ and $F_p$ were significantly higher for successful discharge from the hospital than for unsuccessful, with P=0.0001 and 0.002, respectively.

Figure 9:
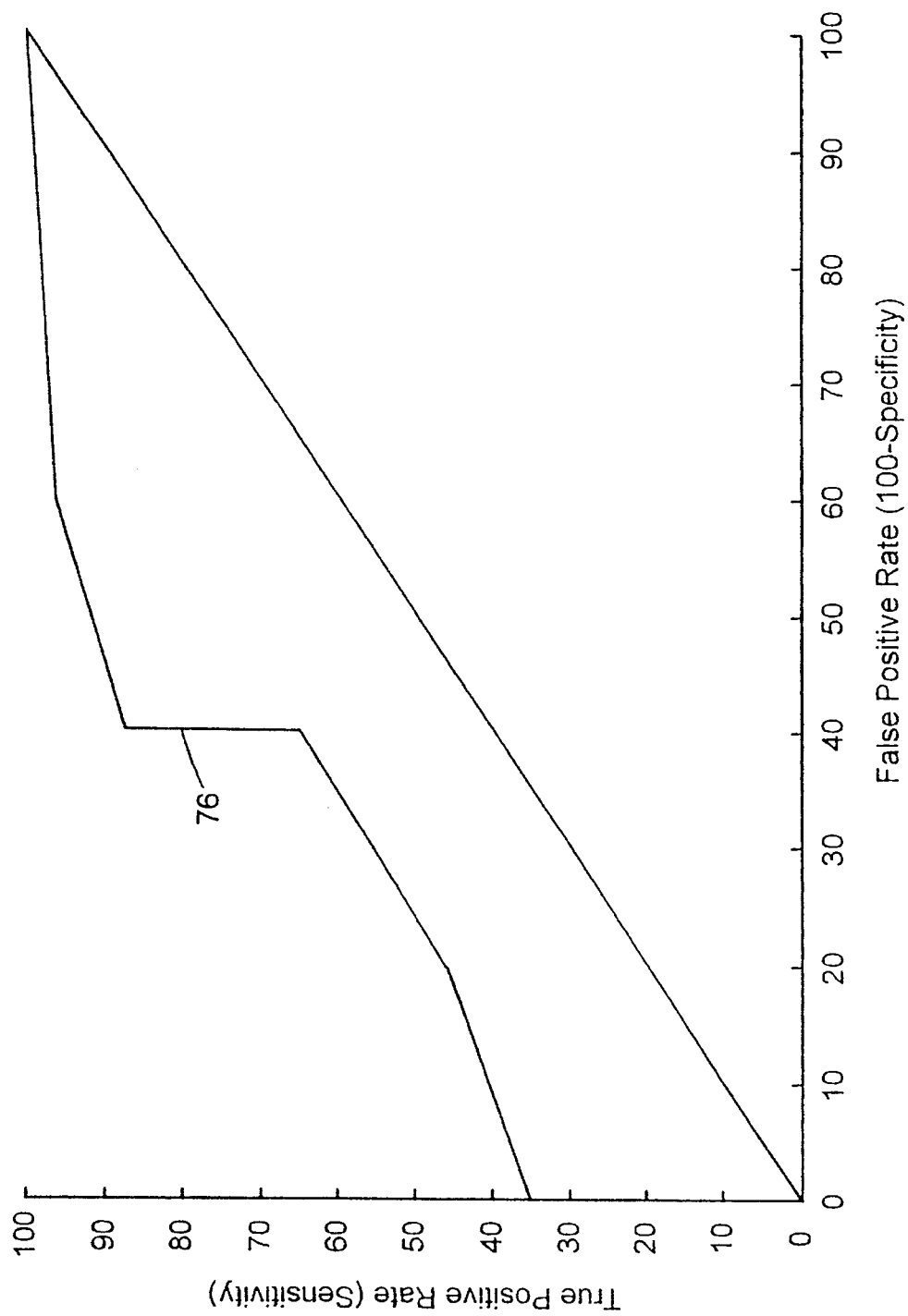
FIG. 9 is a graph illustrating a receiver operating characteristic curve of the centroid frequency of the power spectrum for an outcome wherein return of spontaneous circulation occured at a later time.
Figure 10:
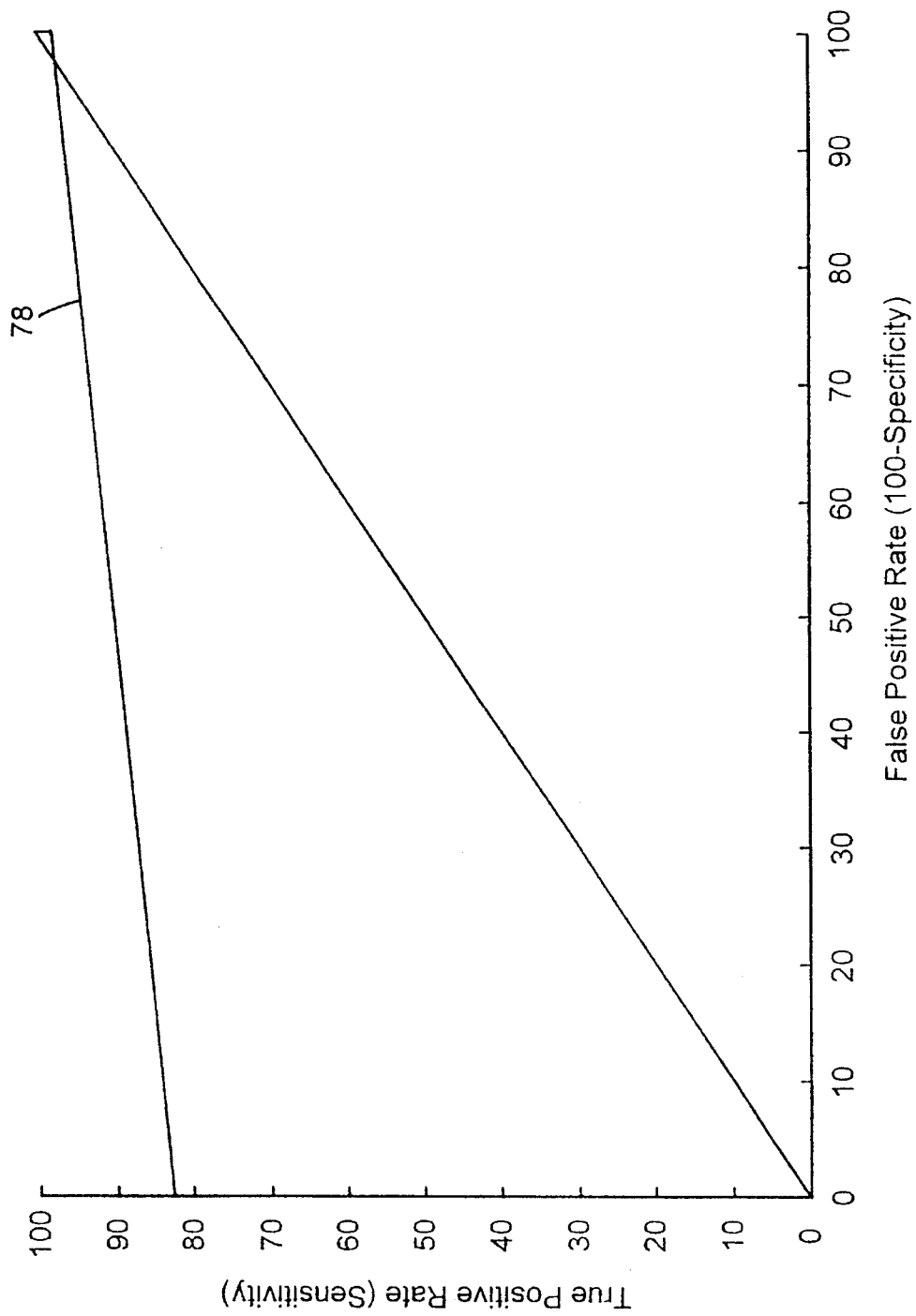
FIG. 10 is a graph illustrating a receiver operating characteristic curve of the peak power frequency of the power spectrum for an outcome wherein return of spontaneous circulation occured at a later time.
Figure 11:
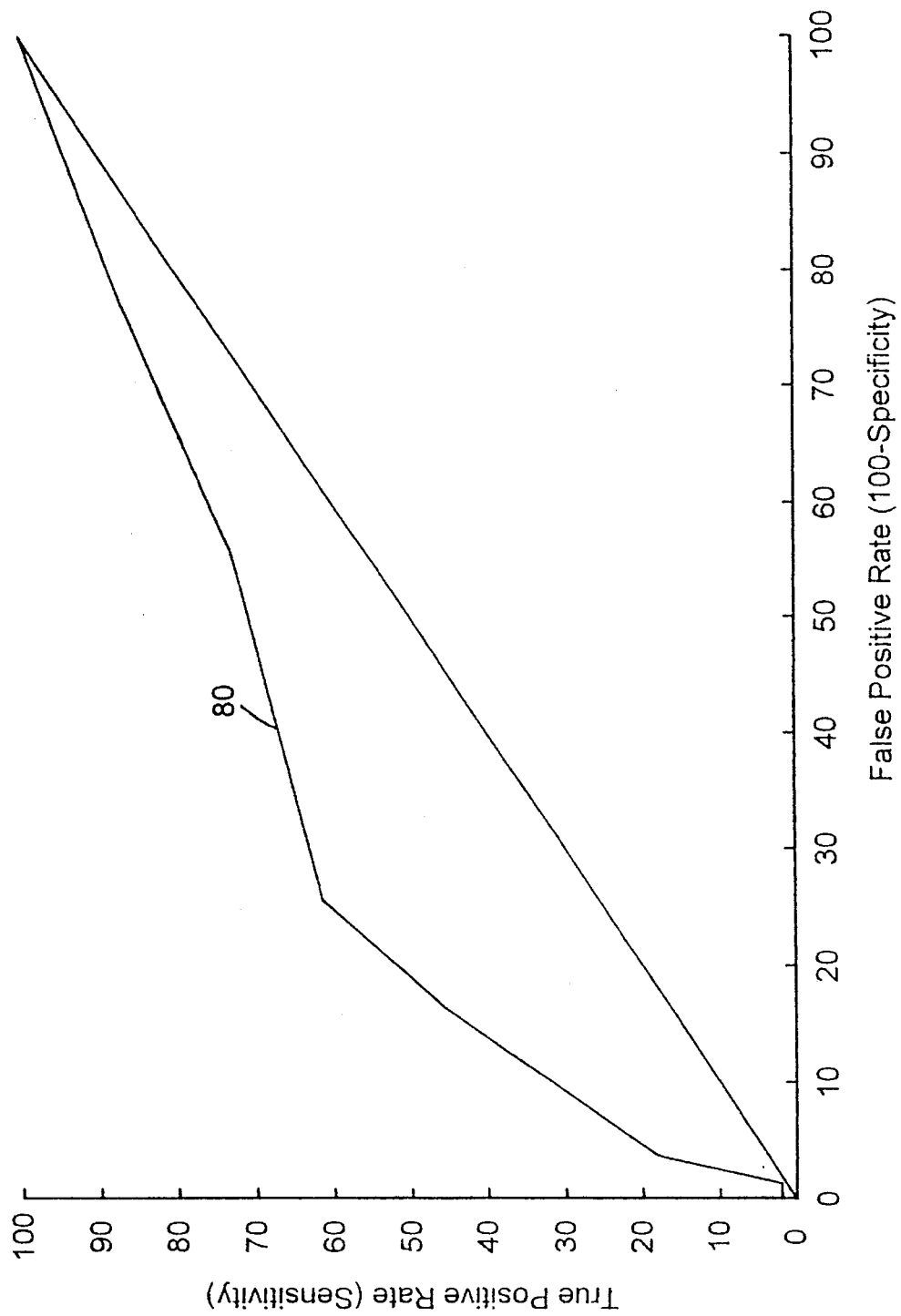
FIG. 11 is a graph illustrating a receiver operating characteristic curve of the centroid frequency of the power spectrum for an outcome of survival until hospital admission.
Figure 12:
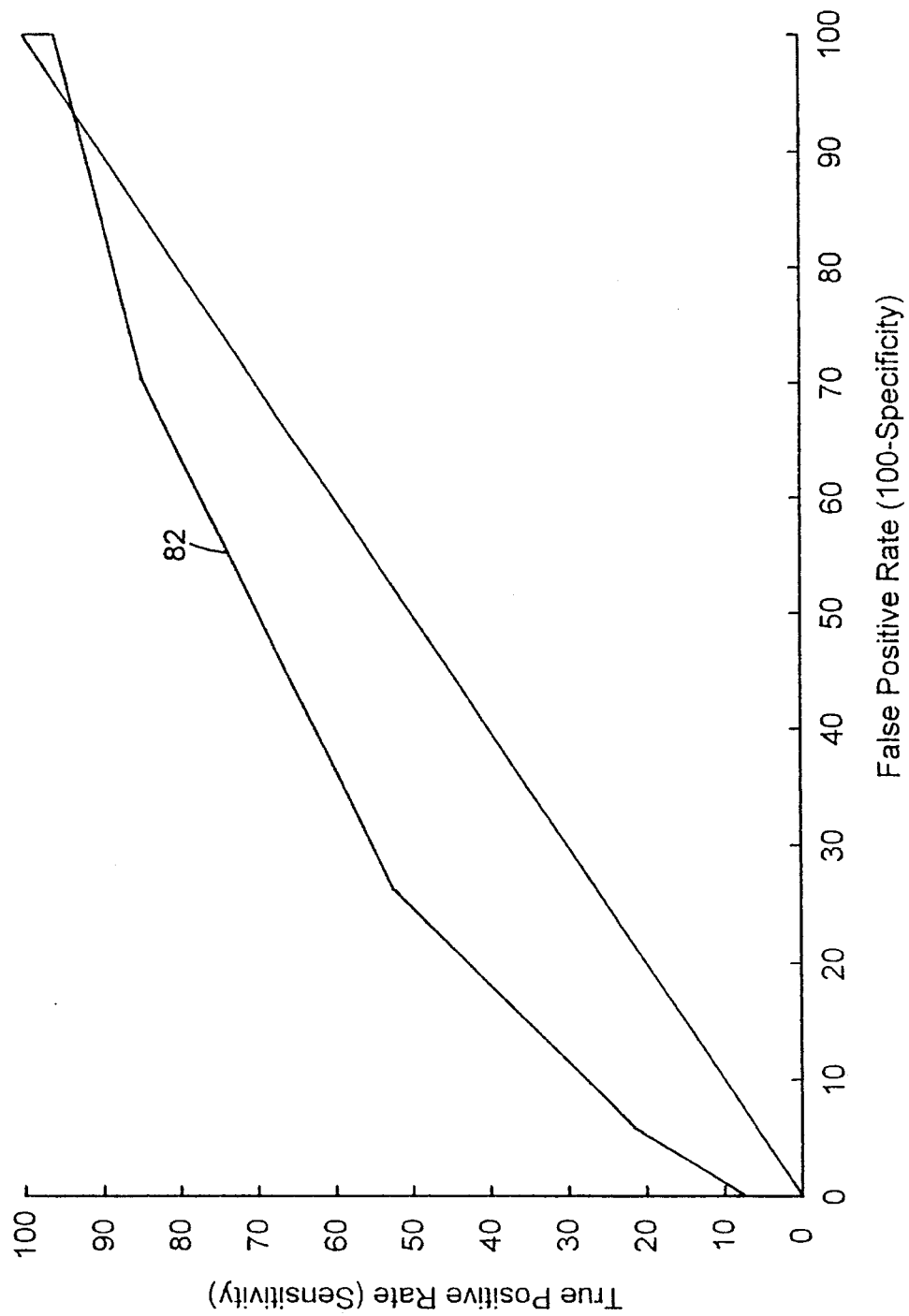
FIG. 12 is a graph illustrating a receiver operating characteristic curve of the peak power frequency of the power spectrum for an outcome of survival until hospital admission.
Figure 13:
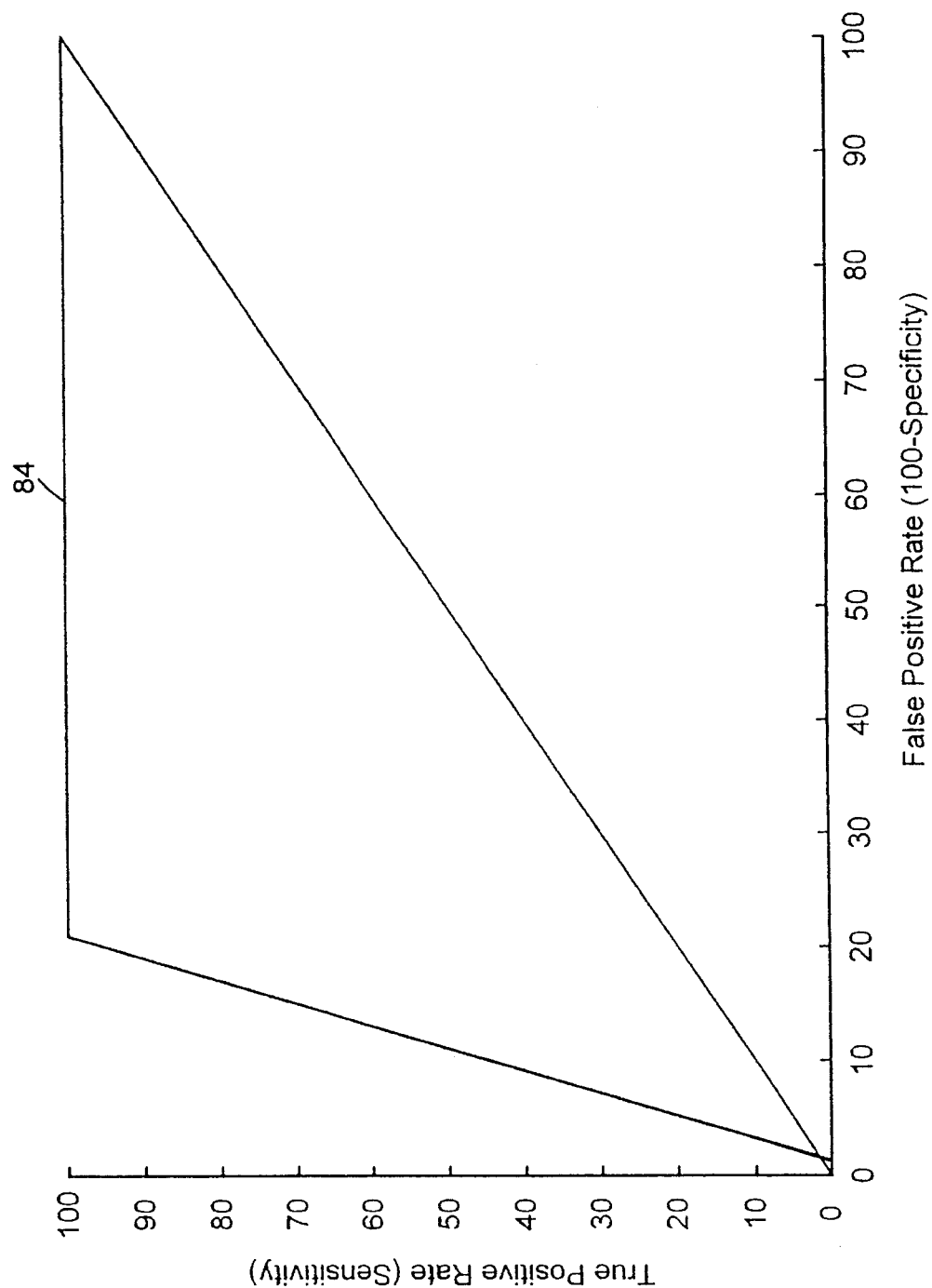
FIG. 13 is a graph illustrating a receiver operating characteristic curve of the centroid frequency of the power spectrum for an outcome of survival until hospital discharge.
Figure 14:
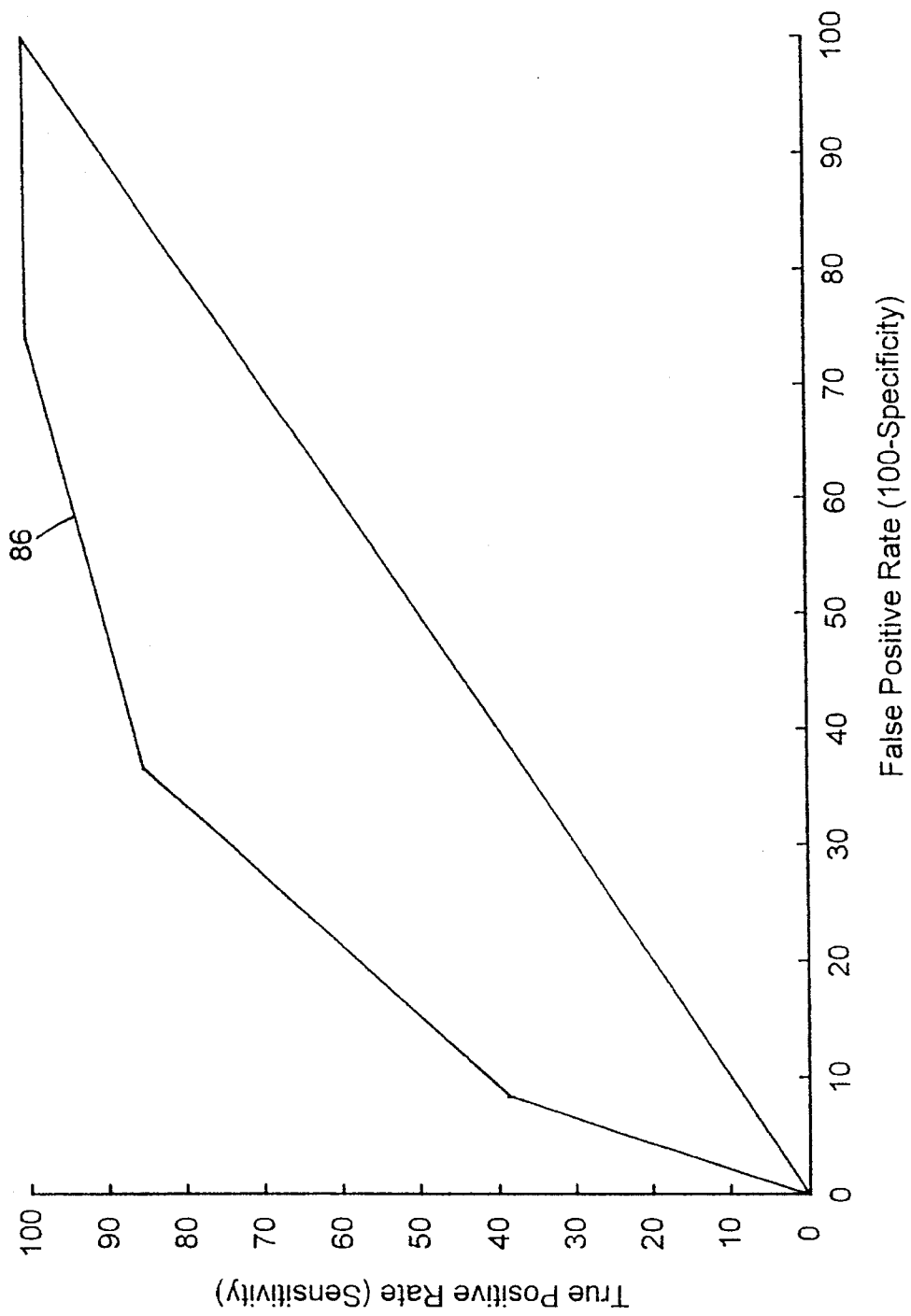
FIG. 14 is a graph illustrating a receiver operating characteristic curve of the peak power frequency of the power spectrum for an outcome of survival until hospital discharge.

An ROC curve 76 of $F_c$ for the outcome of whether the subject ever experienced a return of spontaneous circulation, is illustrated in FIG. 9. The area under curve 76 is 0.767. An ROC curve 78 of the parameter. $F_p$, for the outcome of whether the subject ever experienced a return of spontaneous circulation, is illustrated in FIG. 10. The area under curve 78 is 0.890. An examination of the areas under curves 76 and 78 illustrates the significant predictive value of these parameters for return of spontaneous circulation. An ROC curve 80 of the parameter $F_c$ for the successful outcome of survival to admission to a hospital is illustrated in FIG. 11. The area under curve 80 is 0.656. Likewise, the ROC curve 82 of the parameter $F_p$ for the successful outcome of survival to admission to a hospital is illustrated in FIG. 12. The area under curve 82 is 0.616. An ROC curve 84 of the parameter $F_c$ for the successful outcome of survival to discharge from a hospital is illustrated in FIG. 13 and an ROC curve 86 of the parameter $F_p$ for survival to discharge is illustrated in FIG. 14. The area under curve 84 is 0.886 and the area under curve 86 is 0.835. A review of the areas under curves 80, 82, 84, and 86 illustrates the predictive value of these parameters.

Thus, it is seen that the present invention provides a useful method and apparatus for both guiding interventions for subjects experiencing cardiac arrest as well as predicting the likelihood that particular interventions will be successful. Although the invention has application in treating human subjects in cardiac arrest, it may also be used as a research monitor for evaluating the effect of interventions on human subjects, or used on other animal subjects, in which cardiac arrest is induced. Changes and modifications in the specifically described embodiments can be carried out without departing from the principles of the invention, which is intended to be limited only by the scope of the appended claims, as interpreted according to the principles of patent law including the doctrine of equivalents.

The embodiments of the invention in which an exclusive property or privilege is claimed are defined as follows:

1. A non-invasive method of guiding the administration of therapy to a subject in ventricular fibrillation or asystole, including:

connecting electrodes to the body of the subject and detecting from the electrodes an analog electrical potential which is proportional to the electrical potential generated by the subject's heart;

sampling the analog potential for a selected interval of time to obtain a set of time domain samples;

detecting the power distribution of said electrical potential by transforming said time domain samples to a frequency domain power spectrum;

monitoring and evaluating at least one frequency parameter of said power spectrum that is predictive of a clinically relevant cardiac arrest outcome for the subject, said at least one parameter selected from the group consisting of at least centroid frequency and peak power frequency; and using a monitored evaluation of said selected frequency parameter in administering therapy to the subject.

2. The method of claim 1 wherein said at least one parameter includes both centroid frequency of said power spectrum and peak power frequency of said power spectrum.

3. The method of claim 2 wherein said step of using a monitored evaluation comprises administering said therapy as a function of at least one of said centroid frequency and said peak power frequency being equal to or above a predetermined threshold level.

4. The method of claim 3 wherein said threshold level for said centroid frequency is between approximately 3.86 $H_z$ and approximately 6.12 $H_z$.

5. The method of claim 4 wherein said threshold level for said peak power frequency is between approximately 3.5 $H_z$ and approximately 7.75 $H_z$.

6. The method of claim 3 wherein said threshold level for said peak power frequency is between approximately 3.5 $H_z$ and approximately 7.75 $H_z$.

7. The method of claim 1 wherein said administering therapy includes selecting a therapy protocol as a function of a value of said at least one parameter determined by said evaluation.

8. The method of claim 7 wherein said selecting a therapy protocol includes selecting the type and dosage of a drug.

9. The method of claim 7 wherein said selecting a therapy includes selecting a defibrillation threshold comprising a minimum amount of electrical energy or current for administering a countershock.

10. The method of claim 7 wherein said selecting a therapy includes selecting at least one compression parameter of cardiopulmonary resuscitation from the group consisting of rate, depth, and force of compression.

11. The method of claim 7 wherein said selecting a therapy includes selecting an electrical waveform for administering a countershock.

12. The method of claim 7 wherein said selecting a therapy protocol includes selecting a paddle position for administering a countershock.

13. The method of claim 1 wherein said administering therapy includes titrating said therapy until a predetermined value of said at least one parameter is reached.

14. The method of claim 1 wherein said at least one parameter is predictive of a successful countershock outcome for the subject.

15. The method of claim 1 wherein said at least one parameter is predictive of the subject achieving a return of spontaneous circulation.

16. The method of claim 1 wherein said at least one parameter is predictive of the survival of the subject until at least the time of admission to a medical care facility.

17. The method of claim 1 wherein said at least one parameter is predictive of the survival of the subject to the time of discharge from a medical care facility.

18. The method of claim 1 wherein said at least one parameter includes two particular parameters, and wherein said administering is a function of the said evaluation of each of said two parameters.

19. The method of claim 18 wherein said two parameters include centroid frequency of said power spectrum and peak power frequency of said power spectrum.

20. The method in claim 18 wherein said administering is a function of at least one of said two parameters being equal to or above respective threshold levels.

21. The method in claim 20 wherein said two parameters include centroid frequency of said power spectrum and peak power frequency of said power spectrum and wherein said threshold levels are selected from ranges of between approximately 3.86 $H_z$ and approximately 6.12 $H_z$ and between approximately 3.5 $H_z$ and approximately 7.75 $H_z$, respectively.

22. A non-invasive method of determining the metabolic state of the myocardium of a subject in ventricular fibrillation or asystole, including:
   connecting electrodes to the body of the subject and detecting from the electrodes an analog electrical potential which is proportional to the electrical potential generated by the subject's heart;
   sampling the analog potential for a selected interval of time to obtain a time domain signal;
   detecting the power distribution of said electrical potential by transforming said time domain signal to a frequency domain power spectrum;
   monitoring at least one amplitude parameter of the time-domain signal and at least one frequency parameter of said power spectrum including at least the centroid frequency that is predictive of a clinically relevant cardiac arrest outcome for the subject; and
   resolving said monitored parameters to obtain an indication which is directly indicative of the metabolic state of the myocardium of the subject's heart.

23. The method of claim 22 wherein said at least one frequency parameter includes the centroid frequency of said power spectrum.

24. The method of claim 22 wherein said value is predictive of the outcome of countershock for the subject.

25. The method of claim 22 wherein said value is predictive of the subject achieving a return of spontaneous circulation.

26. The method of claim 22 wherein said value is predictive of the survival of the subject until at least admission to a medical care facility.

27. The method of claim 22 wherein said value is predictive of the survival of the subject to the point of discharge from a medical care facility.

28. An apparatus that non-intrusively provides a clinically useful indicator of the condition of the heart of a subject in ventricular fibrillation or asystole from an electrocardiogram of the heart, said electrocardiogram made up of time domain samples of analog electrical signals, comprising:
   an analyzer for transforming said time domain samples to a frequency domain power spectrum and for determining at least one frequency parameter of said power spectrum that is predictive of a clinically relevant cardiac arrest outcome for the subject, said at least one frequency parameter including the centroid frequency of said frequency domain power spectrum; and
   a processor coupled to said analyzer to resolve said at least one parameter to a clinically useful indicator of a predetermined characteristic of the subject's heart.

29. The apparatus in claim 28 wherein said at least one parameter includes both centroid frequency of said power spectrum and peak power frequency of said power spectrum.

30. The apparatus in claim 29 wherein said processor determines whether at least one of said centroid frequency and said peak power frequency is equal to or above a predetermined threshold.

31. The apparatus in claim 28 wherein said predetermined characteristic of the subject's heart is the metabolic state of the myocardium.

32. The apparatus in claim 28 wherein said at least one parameter includes at least two parameters.

33. The apparatus in claim 32 wherein said at least two parameters includes the centroid frequency and peak power frequency of the power spectrum.

34. The apparatus in claim 33 wherein said processor includes means for determining that at least one of said centroid frequency and peak power frequency are equal to or above respective thresholds.

35. The apparatus of claim 34 wherein said predetermined thresholds are in the range of between approximately 3.86 $H_z$ and approximately 6.12 $H_z$ for said centroid frequency and between approximately 3.5 $H_z$ and approximately 7.75 $H_z$ for said peak power frequency.

36. The apparatus in claim 28 including a display coupled to said processor for displaying said clinically useful indicator.

37. The apparatus in claim 28 including a display coupled to said processor for displaying said at least one parameter.

38. The apparatus in claim 28 including an event marker coupled to said processor for receiving user input designations of the occurrence of events.

39. An apparatus for guiding the administration of therapy to a subject in ventricular fibrillation or asystole from an electrocardiogram of the heart made up of time domain samples of analog electrical potential, comprising:

an analyzer for transforming said time domain samples to a frequency domain power spectrum and for determining a value that is predictive of a clinically relevant cardiac arrest outcome for the subject based on the centroid frequency of said frequency domain power spectrum and the peak power frequency of said frequency domain power spectrum;

a processor coupled to said analyzer; and at least one therapy-administering device coupled to and controlled by said processor for administering therapy to the subject as a function of said determined value.

40. The apparatus in claim 39 wherein said analyzer determines said value by comparing centroid frequency parameters and peak power frequency parameters.

41. The apparatus in claim 40 wherein said at least one therapy-administering device administers therapy if said processor determines that at least one of said centroid frequency and said peak power frequency is equal to or above a respective threshold.

42. The apparatus in claim 41 wherein said respective threshold of said centroid frequency is in the range of between approximately 3.86 $H_z$ and approximately 6.12 $H_z$, and said respective threshold of said peak power frequency is in the range of between approximately 3.5 $H_z$ and approximately 7.75 $H_z$.

43. The apparatus in claim 39 wherein said at least one therapy-administering device includes a defibrillator for administering a countershock.

44. The apparatus in claim 39 wherein said at least one therapy-administering device includes a resuscitator for administering cardiopulmonary resuscitation.

* * * * *